United States Patent [19]

Howell

[11] Patent Number: 5,165,929

[45] Date of Patent: Nov. 24, 1992

[54] FUNGAL ANT KILLER

[76] Inventor: William G. Howell, 4143 Miraflores La., Tallahassee, Fla. 32303

[21] Appl. No.: 740,933

[22] Filed: Sep. 10, 1991

[51] Int. Cl.$^5$ .............................................. A61K 35/70
[52] U.S. Cl. ................................................. 424/93 Q
[58] Field of Search ................................ 424/93, 93 Q Primary Examiner—Douglas W. Robinson
Assistant Examiner—Jean C. Witz

[57] ABSTRACT

The fungus, *Rhizopus nigricans,* can be used as an insecticide for use in killing ants in the order Hymenoptera. When this fungus is brought into or put into an ant hive, it kills the ants within a few days.

1 Claim, No Drawings

FUNGAL ANT KILLER

SUMMARY OF THE INVENTION

When a member of the fungal order of Mucorales is applied to a member of the order Hymenoptera insect groups' hive, destruction of the hive occurs. The mold is grown and when inserted into the hive or is brought into the hive by the insects, the hive is destroyed.

DETAILED DESCRIPTION

The process involves applying fungal material from a fungus in the Mucorales order into or onto a hive, or providing the fungus near or on a hive on a food source for the insects and having the insects bring the fungus into the hive of insects in the order Hymenoptera for the purpose of killing the hive. The fungus is grown in a 1-liter container with cocoa powder mixed with water. This substrate is inoculated with the fungus *Rhizopus nigricans* or other fungus in the order Mucorales, which then spreads over the surface of the substrate in approximately 48 hours. The fungus is then separated from the substrate and mixed with various combinations of cocoa powder or other nutrients and water to apply to the hives. The application can be by the following:

mix the fungus with water and apply to the hive;

mix the fungus with water and nutrients for the fungus and apply to the hive;

mix the fungus with nutrients and apply to the hive; and mix the fungus with nutrients and place it near the hive.

I claim:

1. A method of killing ants in hives comprising administering to an ant hive or locus thereof an effective amount of a composition comprising fungus from the Genus Rhizopus.

* * * * *